US011119308B2

United States Patent
Wieters

(10) Patent No.: US 11,119,308 B2
(45) Date of Patent: Sep. 14, 2021

(54) VIDEO ENDOSCOPE

(71) Applicant: OLYMPUS WINTER & IBE GMBH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 16/961,530

(22) PCT Filed: Dec. 20, 2018

(86) PCT No.: PCT/EP2018/086259
§ 371 (c)(1),
(2) Date: Jul. 10, 2020

(87) PCT Pub. No.: WO2019/137785
PCT Pub. Date: Jul. 18, 2019

(65) Prior Publication Data
US 2020/0355907 A1   Nov. 12, 2020

(30) Foreign Application Priority Data

Jan. 10, 2018   (DE) .......................... 102018100481.8

(51) Int. Cl.
*G02B 23/24* (2006.01)
*A61B 1/05* (2006.01)
*H04N 5/225* (2006.01)

(52) U.S. Cl.
CPC ....... *G02B 23/243* (2013.01); *G02B 23/2476* (2013.01); *A61B 1/05* (2013.01); *H04N 5/2252* (2013.01); *H04N 2005/2255* (2013.01)

(58) Field of Classification Search
CPC .............. G02B 23/243; G02B 23/2476; H04N 5/2252; A61B 1/05; A61B 1/0623; A61B 1/0676; A61B 1/045
See application file for complete search history.

(56) References Cited

U.S. PATENT DOCUMENTS 5,575,756 A * 11/1996 Karasawa .......... A61B 1/00068
                                                          600/121
9,661,988 B2 * 5/2017 Dahmen ............ G02B 23/2476
(Continued)

FOREIGN PATENT DOCUMENTS

DE   102004044119 A1   3/2006
DE   10201607275 A1   11/2017
(Continued)

OTHER PUBLICATIONS

International Search Report and Written Opinion dated Apr. 5, 2019 issued in PCT/EP2018/086259, with partial translation.
(Continued)

*Primary Examiner* — Rowina J Cattungal
(74) *Attorney, Agent, or Firm* — Scully, Scott, Murphy & Presser, P.C.

(57) ABSTRACT

A video endoscope including: an elongated shaft having distal and proximal ends; an objective lens arranged in the shaft; and an image sensor arranged proximally to the objective lens; wherein the objective lens includes distal and proximal objective lens assemblies; the image sensor rotates about an axis of the shaft relative to the distal objective lens assembly which is arranged in an outer tube; a torque for rotating the image sensor is transmitted by an inner tube, which is arranged in the outer tube, the inner tube being rotatably fixed and axially slidably connected to a frame receiving the image sensor, the inner tube and the frame each including coupling portions that engage coaxially; one the coupling portions includes cut-outs extending parallel to the axis; and another includes elastic protrusions, the elastic protrusions extending toward and engage in a corresponding cut-out.

13 Claims, 3 Drawing Sheets

(56) References Cited

U.S. PATENT DOCUMENTS

| | | | | |
|---|---|---|---|---|
| 2006/0058581 A1* | 3/2006 | Hanke | ............... | G02B 23/2423 |
| | | | | 600/109 |
| 2007/0112254 A1* | 5/2007 | Weigel | .................... | A61B 1/05 |
| | | | | 600/137 |
| 2014/0128674 A1* | 5/2014 | Wieters | ................ | H01F 7/0252 |
| | | | | 600/109 |
| 2014/0128679 A1* | 5/2014 | Wieters | ................... | A61B 1/05 |
| | | | | 600/170 |
| 2017/0347861 A1* | 12/2017 | Deutschendorf | .... | A61B 1/0011 |

FOREIGN PATENT DOCUMENTS

| EP | 1787570 A1 | 5/2007 |
|---|---|---|
| WO | WO 2013/007356 A1 | 1/2013 |

OTHER PUBLICATIONS

German Office Action dated Oct. 29, 2018 issued in DE 10 2018 100 481.8.

* cited by examiner

VIDEO ENDOSCOPE

CROSS-REFERENCE TO RELATED APPLICATION

The present application is based upon and claims the benefit of priority from PCT/EP2018/086259 filed on Dec. 20, 2018, which claims benefit to DE 10 2018 100 481.8 filed on Jan. 10, 2018, the entire contents of each of which are incorporated herein by reference.

BACKGROUND

Field

The present disclosure relates to an endoscope and more particularly to a video endoscope comprising an elongated shaft having a distal end and a proximal end, an objective lens arranged at the distal end of the shaft and at least one image sensor arranged proximally relative to the objective lens, wherein the objective lens has a distal objective lens assembly as well as a proximal objective lens assembly, wherein the image sensor, optionally together with the proximal objective lens assembly, can be rotated about the longitudinal axis of the shaft relative to the distal objective lens assembly, the distal objective lens assembly is arranged in an outer tube, and a torque for rotating the image sensor and optionally the proximal objective lens assembly relative to the distal objective lens assembly is transmitted by means of an inner tube, which is arranged in the outer tube and which is connected for conjoint rotation to a frame housing the image sensor and optionally proximal objective lens assembly.

Prior Art

Video endoscopes are used in medicine to examine and/or treat areas in a patient that are difficult to access. To this purpose, they have an elongated shaft whose distal end is guided to the area to be examined.

A video camera, whose signal is transmitted to the proximal end of the shaft and out of the endoscope, is arranged at the distal end of the shaft. The signal is then transmitted to a monitor and represented. The video camera of a video endoscope comprises an objective lens and an image sensor, which may be configured as a CCD or CMOS chip, for example.

The objective lens of a video endoscope is often configured such that it has a viewing direction that differs from that of the longitudinal axis of the shaft. The term viewing direction refers here to the optical axis of the objective lens that is on the objective side. To this purpose, the objective lens may comprise a prism assembly. Corresponding video endoscopes are also referred to as endoscopes with a lateral viewing direction.

Video endoscopes with a lateral viewing direction make it possible to cover a particularly large field of vision when the video endoscope is rotated about the longitudinal axis of the shaft. This results in the problem, however, that the video sensor rotates as well when the video endoscope is rotated. This causes the horizontal position of the image, which is shown on a monitor, for example, to be lost, which may cause physicians to lose their orientation on the image.

To prevent this, the image sensor is integrated in the video endoscope in such a way that it is rotatable about the longitudinal axis of the shaft. If now the video endoscope is rotated, the image sensor can be rotated in the opposite direction so that it maintains its original orientation. In doing so, the horizontal position of the image is maintained as well.

For technical reasons, the objective lens is often divided and is comprised of a distal objective lens assembly, which contains the prism assembly, and a proximal objective lens assembly. The two objective lens assemblies can be rotated against each other, wherein the distal objective lens assembly is rotatably fixed with respect to the shaft of the video endoscope, while the proximal objective lens assembly is rotatable relative to the shaft together with the image sensor. In that case, the distal and the proximal objective lens assemblies are connected by means of an axially and radially acting bearing.

A torque required to rotate the objective lens assemblies against each other is generally applied at the proximal end of the video endoscope, for example with a rotating swivel, and transferred by means of an inner tube to a frame, which accommodates the image sensor and, if applicable, the proximal objective lens assembly. The distal objective lens assembly is arranged in an outer tube which encompasses the inner tube. At the proximal end of the inner tube and the outer tube, these are generally supposed against each other by means of a bearing. The bearing is mounted to a bearing sleeve, which is fastened to the proximal end of the outer tube in a rotationally fixed manner.

To simplify the assembly of the video endoscope and/or to lighten the load placed on the bearing by the inert forces of the tube and the components connected to it, the inner tube may be connected to the proximal objective lens assembly in a rotatably fixed but axially slidable manner.

The creation of the rotatably fixed and possibly slidable connection between the inner tube and the proximal objective lens assembly and/or between the outer tube and the bearing sleeve is not that easy. To ensure an easy assembly and an axial sliding motion, the connection must have a loose fit. As a result, however, the torque cannot be transmitted without any play, which can result in slight variations during the operation of the video endoscope in the horizontal position of the image, which is disruptive.

SUMMARY

An object is therefore to provide a video endoscope that is improved with respect to the problem described.

Such object can be achieved by a video endoscope with an elongated shaft having a distal end and a proximal end, an objective lens arranged at the distal end of the shaft and at least one image sensor arranged proximally relative to the objective lens, wherein the objective lens has a distal objective lens assembly and a proximal objective lens assembly, the image sensor, optionally together with the proximal objective lens assembly, can be rotated about a longitudinal axis of the shaft relative to the distal objective lens assembly, the distal objective assembly is arranged in an outer tube, and a torque for rotating the image sensor and optionally the proximal objective lens assembly relative to the distal objective lens assembly is transmitted by means of an inner tube arranged in the outer tube, which is rotatably fixed and axially slidably connected to a frame receiving the image sensor and optionally the proximal objective lens assembly, Wherein the inner tube and the proximal objective lens assembly have coupling portions that engage one in the other coaxially, a first of the coupling portions of the frame and the inner tube has at least two cut-outs extending parallel to the longitudinal axis of the shaft and a second of the coupling portions of the frame and the inner tube has at least two elastic protrusions, which extend toward the first coupling portion and engage in the cut-outs.

Such objective can be achieved by a video endoscope comprising an elongated shaft having a distal end and a proximal end, an objective lens arranged at the distal end of the shaft and at least one image sensor arranged proximally relative to the objective lens, wherein the objective lens has a distal objective lens assembly and a proximal objective lens assembly, the image sensor, optionally together with the proximal objective lens assembly, can be rotated about a longitudinal axis of the shaft relative to the distal objective lens assembly, the distal objective assembly is arranged in an outer tube, a torque for rotating the image sensor and optionally the proximal objective lens assembly relative to the distal objective lens assembly is transmitted by means of an inner tube arranged in the outer tube, which is connected to a frame, which holds the image sensor and optionally the proximal objective lens assembly and wherein the outer tube and the inner tube are supported against each other at the proximal ends thereof by means of a bearing, which is arranged in a bearing sleeve fastened to the proximal end of the outer tube, wherein the outer tube and the bearing sleeve have coupling portions that engage one in the other coaxially with a first of the coupling portions of the outer tube and the bearing sleeve having at least two cut-outs extending parallel to the longitudinal axis of the shaft and a second of the coupling portions of the outer tube and the bearing sleeve having at least two elastic protrusions, which extend toward the first coupling portion and engage in the cut-outs.

The elastic protrusions of the first coupling portions can each elastically engage in the cut-outs of the second coupling portions and thus reduce the play of the coupling significantly. At the same time, the axial sliding motion of the connection is ensured.

as Also provided is an assembly of the video endo scope that comprises at least one optical element of the objective lens. An objective lens assembly may also comprise non-optical elements such as mechanical frames, electromagnetic actuators, bearings or the like.

The cut-outs can be provided on the coupling portion of the frame and/or the bearing sleeve while the protrusions can be provided on the coupling region of the inner tube and/or the outer tube. Inverted embodiments in which the cut-outs can be provided on the coupling region of the inner tube and/or the outer tube and the protrusions can be provided on the coupling portion of the frame and/or the bearing sleeve are, however, possible as well.

The aforementioned aspects can be used in a video endoscope either individually or together.

In an embodiment, the elastic protrusions can be flexible tongues cut from the inner and/or the outer tube. In this case, the forming of the respective protrusions can be provided by an open contour cut into the tube, for example by means of a laser beam. In the process, the cut-out flexible tongue remains connected to the tube at its base. Then, the flexible tongue is plastically deformed so that it has a resting position that deviates from the contour of the tube.

The flexible tongues can be cut in such a way that their base first dips into the objective lens-side and/or the bearing sleeve-side coupling portion when it is integrated into the objective assembly and/or the bearing sleeve. In this process, the flexible tongues can be deflected by the objective lens-side and/or bearing sleeve-side coupling portion and spring back into the cut-outs.

According to an embodiment, the flexible tongues can have a trapezoid structure. A trapezoid structure is a structure in which the width of the flexible tongue decreases from a base where the flexible tongue is connected to the tube to a tip, which is freely movable against the spring force of the flexible tongue.

A flexible tongue configured in such a manner can first dip into a cut-out with its tip and is then pressed in the direction of the cut-out by the spring force of the flexible tongue until the width of the flexible tongue corresponds at a contact point with the cut-out exactly the width of the cut-out. This ensures a coupling that is free of any play.

In an embodiment, the number of cut-outs and the number of protrusions can be the same so that each protrusion engages in a cut-out. To ensure an even transmission of the torque, the protrusions and the cut-outs can be evenly distributed across the circumference of the coupling portions, for example in a 2×180° arrangement or in a 3×120° arrangement.

In another embodiment, the number of the protrusions can be greater than the number of the cut-outs. Furthermore, the excess protrusions may form an electrical contact between the outer tube and the bearing sleeve.

Such configuration can be useful where the outer tube and the bearing sleeve act as an electromagnetic shield at the same time. In this case, a good electric contact is required at the connection point, which a contact between the protrusions and the cut-outs with a small surface cannot guarantee.

An inner tube is a tube which is arranged within at least one further tube. The inner tube does not, however, have to be an innermost tube of the video endoscope. The inner tube can be connected with a rotating swivel of the video endoscope through a magnetic coupling, by means of which the orientation of the image sensor is kept constant when the video endoscope is rotated.

An outer tube is a tube within which at least one further tube is arranged. The outer tube does not have to be the outermost tube of the video endoscope. The outer tube can be rotatably coupled to the shaft of the video endoscope and thus accordingly take the proximal objective assembly with it when the video endoscope is rotated about the longitudinal axis of the shaft.

BRIEF DESCRIPTION OF THE DRAWINGS

Below, the embodiments will be explained in further detail with the help of some exemplary representations. These representations are only intended to contribute to a better understanding of the embodiments and do not delimit the general concept of the invention.

The figures show the following.

DETAILED DESCRIPTION

Figure 1:
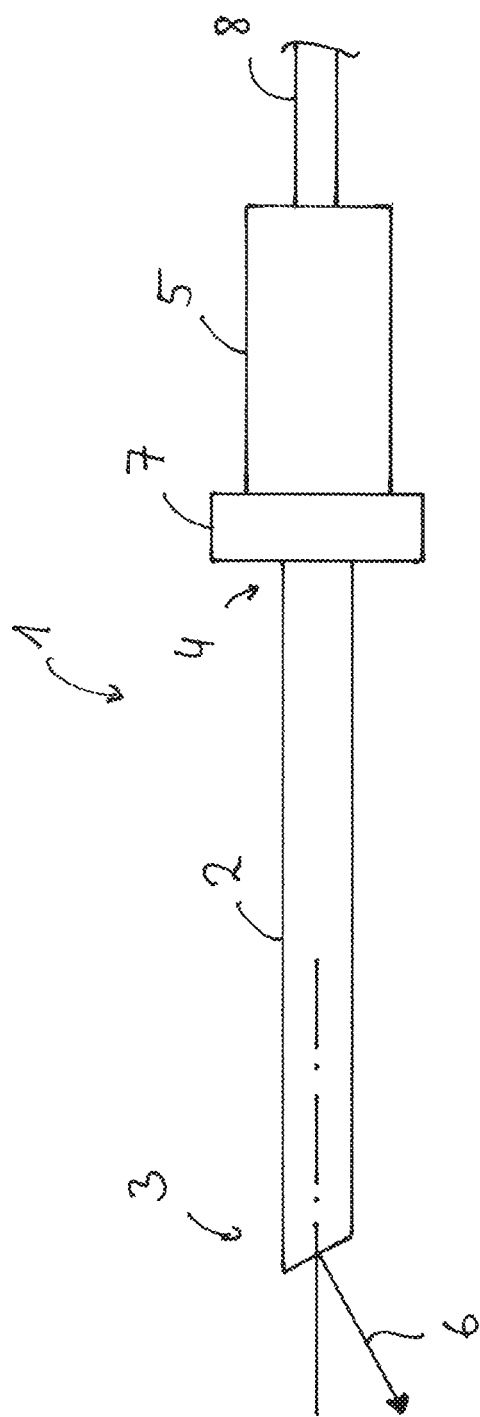
FIG. 1 illustrates a video endoscope.

FIG. 1 shows a video endoscope 1. The video endoscope 1 comprises an elongated shaft 2 having a distal end 3 and a proximal end 4. A handle 5 is arranged at the proximal end 4 of the shaft 2, by means of which the video endoscope 1 can be held and operated.

At the distal end 3 of the shaft 2, an objective lens is arranged, which is not shown, but whose viewing direction points in the direction of the arrow 6. By rotating the video endoscope 1, the viewing direction of the objective lens can be rotated about its longitudinal axis. A rotating swivel 7 helps control the horizontal position of an image taken by the video endoscope 1. The video signals generated by the video endoscope 1 are transmitted through a cable 8.

Figure 2:
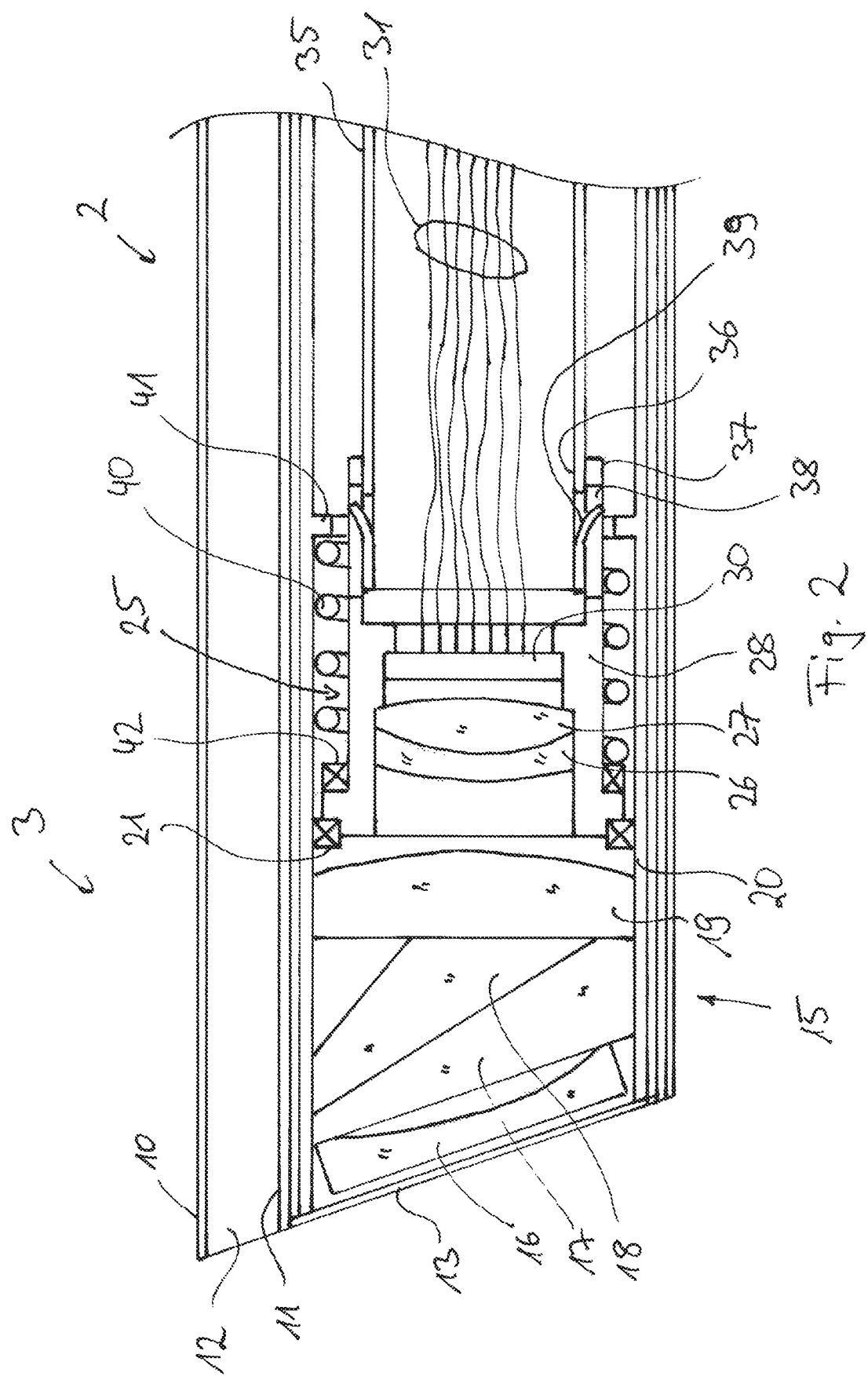
FIG. 2 illustrates the distal end of a video endoscope,
FIG. 3 illustrate the proximal end of the video endoscope.

The inner structure of the distal end 3 of the shaft 2 is shown in further detail in FIG. 2. Between an outer cladding tube 10 and a fiber tube 11 eccentrically arranged in the cladding tube 10, fiber optics 12 are arranged, by means of which the field of vision of the video endoscope 1 can be illuminated. The distal end of the fiber tube 11 is closed by a window 13, which is inserted into the fiber tube 11 in a hermetically tight manner.

Within the fiber tube, close to the window 13, a distal objective lens assembly 15 is provided, which consists of a plurality of optical elements 16, 17, 18, 19, which are held in an outer tube 20. In the example shown, the optical elements 16, 17, 18, 19 are a meniscus lens 16, two prisms 17, 18 and a positive lens 19. Proximal from the distal objective lens assembly, a radially and axially acting bearing 21 is provided, which supports a proximal objective lens assembly 25. The proximal objective lens assembly, in turn, comprises optical elements 26, 27, which are received in a frame 28. In the example shown, the optical elements 26, 27 are two lenses that together form an achromat.

The distal objective lens assembly 15 and the proximal objective lens assembly 25 together form the objective lens of the video endo scope 1.

An electronic image sensor 30 is arranged in the frame 28 as well. It converts an image generated by the objective lens into electrical signals, which are transmitted through cables 31 in the direction of the proximal end of the video endoscope 1.

To maintain the horizontal position of the image when the video endoscope 1 is rotated about a longitudinal axis of the shaft 2, the proximal objective lens assembly 25 may be rotated together with the image sensor relative to the distal objective lens assembly 15. To this purpose, an inner tube 35 is connected to the frame 28 in a rotatably fixed and axially slidable manner.

The inner tube 35 coaxially engages with a coupling portion 36 in a coupling portion 37 of the frame 28. The coupling portion 37 of the frame 28 provides cut-outs 38 in which elastic protrusions of the inner tube 35 engage. The elastic protrusions are flexible tongues 39 that were cut out from the inner tube 35 and that are plastically pre-bent in the outer direction after they are cut out. To assemble the inner tube 35 with the frame 28, the flexible tongues 39 are elastically bent inward and then spring back into the cut-outs 38.

Alternative to the embodiment shown, the frame 28 may comprise elastic protrusions, which engage in cut-outs of the inner tube 35.

To ensure a play-free rotational movement of the inner tube 35 together with the frame 28, the flexible tongues 39 have a trapezoid cross-section, i.e. they taper from the proximal to the distal direction. The maximum width of the flexible tongues 39 is greater than the width of the cut-outs 38. In that case, the flexible grooves dip so far into the cut-outs 38 until they come in a play-free contact with them.

A spring 40 presses the frame 28 against the bearing 21, so that there is no axial play between the distal and the proximal objective lens assembly. To this purpose, the spring 40 is supported by a shoulder 41 of the outer tube. A further bearing 42 may be provided between the spring 40 and the frame 28. The bearings 21, 42 can be ceramic slide bearings.

The axial movability of the inner tube 35 in the frame 28 prevents inert axial forces, which might be transferred via the inner tube 35, from acting on the bearings 21, 42.

Figure 3:
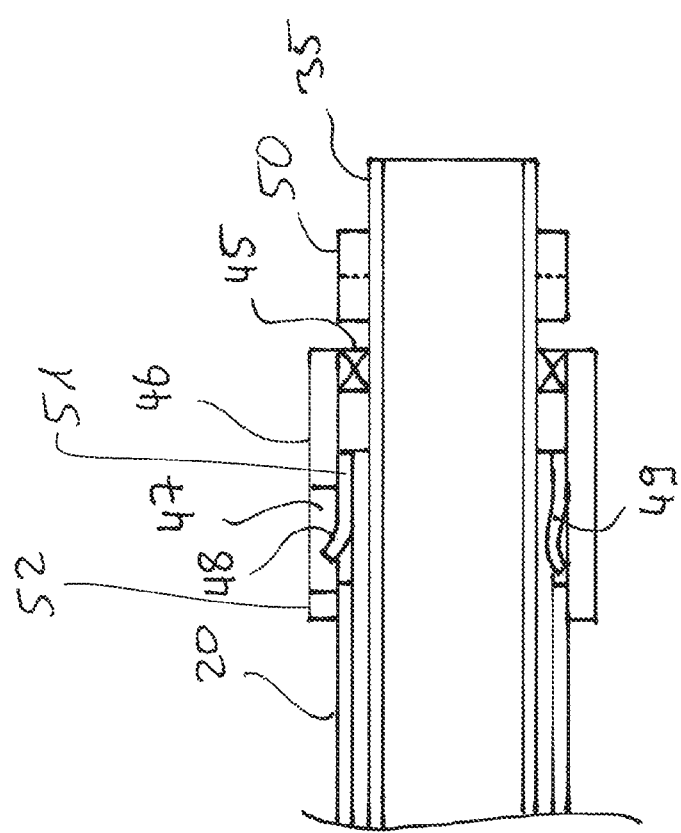

FIG. 3 shows a portion of a proximal section of the video endoscope 1. In this section, the outer tube 20 and the inner tube 35 are supported against each other by a radially acting bearing 45.

The bearing 45 is fastened in a bearing sleeve 46, which, in turn, is fastened at the proximal end of the outer tube 20. The bearing sleeve 46 is fastened to the outer tube 20 in the same way the frame 28 is fastened to the inner tube 35. To this purpose, the bearing sleeve 46 has cut-outs 47, which are engage by elastic protrusions of the outer tube 20. In the example shown, the protrusions of the outer tube are flexible tongues 48 that were cut out from the outer tube and that are plastically pre-bent in the outward direction. To insert the outer tube 20 into the bearing sleeve 46, the flexible tongues are elastically bent inward so that they spring back into the cut-outs 47. To ensure a play-free connection, the flexible tongues 48 have a trapezoid shape as well.

The area of the outer tube 20 that overlaps with the bearing sleeve 46 forms the respective coupling regions 51, 52.

As an alternative to the embodiment shown, the bearing sleeve 46 may comprise elastic protrusions that engage in the cut-outs of the outer tube 20.

In the example shown, the outer tube 20 serves as an electromagnetic shield of the image sensor 30 as well as the cables 31. The deflection of the field occurs by means of the bearing sleeve 46, which is why the outer tube 20 and the bearing sleeve 46 must have a good electrical contact. Such a contact cannot be provided by the small-surface contact of the flexible tongues 48 with the cut-outs 47.

To create the electrical contact, further flexible tongues 49 are cut out from the outer tube 20, which are also plastically pre-bent in the outward direction. These flexible tongues 49 do not, however, engage in cut-outs but push against the inner surface of the bearing sleeve 46. This provides a secure contact in a simple manner.

The flexible tongues 49 and/or the inner surface of the bearing sleeve 46 can be gold-plated or coated with any other contact-promoting material to improve the contact that is established.

Magnets 50 are arranged on the inner tube proximal from the bearing 45. They are part of a magnetic coupling, which is not shown in further detail. By means of the magnetic coupling, the inner tube 35 can be rotated against the outer tube 20, for example by means of a rotating swivel 7.

Figure 4:
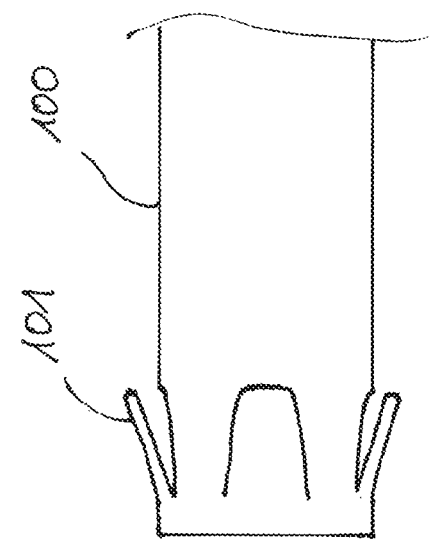
FIG. 4 illustrates a tube with cut-out flexible tongues.

FIG. 4 shows a tube 100 from the contour of which flexible tongues 101 are cut. It may be an outer tube or an inner tube.

In the exemplary embodiments above, the connections are shown in such a manner that the tube is inserted into the coupling portion of the objective assembly and/or the bearing sleeve. It is, of course, also possible to provide the tube with a larger diameter so that the tube overlaps the objective assembly and/or the bearing sleeve. In this case, the flexible tongues must, of course, be pre-bent in the inward direction.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:
1. A video endoscope comprising:
an elongated shaft having a distal end and a proximal end;

an objective lens arranged at the distal end of the shaft; and at least one image sensor arranged proximally relative to the objective lens;

wherein:

the objective lens comprises a distal objective lens assembly and a proximal objective lens assembly;

at least the image sensor is rotatable about a longitudinal axis of the shaft relative to the distal objective lens assembly;

the distal objective lens assembly is arranged in an outer tube;

a torque for rotating the image sensor relative to the distal objective lens assembly is transmitted by an inner tube, the inner tube being arranged in the outer tube, the inner tube being rotatably fixed and axially slidably connected to a frame receiving the image sensor, the inner tube and the frame each comprising coupling portions that engage coaxially;

a first of the coupling portions of one of the frame and the inner tube comprises at least two cut-outs extending parallel to the longitudinal axis of the shaft; and a second of the coupling portions of an other of the frame and the inner tube comprises at least two elastic protrusions, the at least two elastic protrusions each extending toward and engage in a corresponding one of the at least two cut-outs.

2. The video endoscope according to claim 1, wherein the elastic protrusions are elastic tongues cut from the inner and/or the outer tube.

3. The video endoscope according to claim 2, wherein the elastic tongues have a trapezoid shape structure.

4. The video endoscope according to claim 1, wherein the number of cut-outs correspond to the number of protrusions.

5. The video endoscope according to claim 1, wherein the number of protrusions is greater than the number of cut-outs.

6. The video endoscope according to claim 1, wherein the image sensor together with the proximal objective lens assembly are rotatable about the longitudinal axis of the shaft relative to the distal objective lens assembly.

7. A video endoscope comprising:

an elongate shaft having a distal end and a proximal end;

an objective lens arranged at the distal end of the shaft; and at least one image sensor arranged proximally relative to the objective lens;

wherein the objective lens comprises a distal objective lens assembly and a proximal objective lens assembly;

the image sensor is rotatable about a longitudinal axis of the shaft relative to the distal objective lens assembly;

the distal objective lens assembly is arranged in an outer tube;

a torque for rotating the image sensor relative to the distal objective lens assembly is transmitted by an inner tube, the inner tube being arranged in the outer tube, the inner tube being connected to a frame receiving the image sensor;

the outer tube and the inner tube are supported against each other at proximal ends thereof by a bearing, the bearing being arranged in a bearing sleeve fastened to the proximal end of the outer tube;

the outer tube and the bearing sleeve each comprising coupling portions that engage coaxially;

a first of the coupling portions of one of the outer tube and the bearing sleeve comprising at least two cut-outs extending parallel to the longitudinal axis of the shaft; and a second of the coupling portions of an other of the outer tube and the bearing sleeve comprises at least two elastic protrusions, the at least two elastic protrusions each extending toward and engage in a corresponding one of the at least two cut-outs.

8. The video endoscope according to claim 7, wherein the number of protrusions is greater than the number of cut-outs such that at least one protrusion is an excess protrusion, and the excess protrusion forms an electrical contact between the outer tube and the bearing sleeve.

9. The video endoscope according to claim 7, wherein the image sensor-together with the proximal objective lens assembly are rotatable about the longitudinal axis of the shaft relative to the distal objective lens assembly.

10. The video endoscope according to claim 7, wherein the elastic protrusions are elastic tongues cut from the inner and/or the outer tube.

11. The video endoscope according to claim 10, wherein the elastic tongues have a trapezoid shape.

12. The video endoscope according to claim 7, wherein the number of cut-outs correspond to the number of protrusions.

13. The video endoscope according to claim 7, wherein the number of protrusions is greater than the number of cut-outs.

* * * * *